US008735067B2

(12) United States Patent
Zhang et al.

(10) Patent No.: US 8,735,067 B2
(45) Date of Patent: May 27, 2014

(54) ASYMMETRIC PCR AMPLIFICATION, ITS SPECIAL PRIMER AND APPLICATION

(75) Inventors: Zhiwei Zhang, Beijing (CN); Can Wang, Beijing (CN); Lingxiang Zhu, Beijing (CN); Qiong Zhang, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 1481 days.

(21) Appl. No.: 11/661,069

(22) PCT Filed: Nov. 22, 2004

(86) PCT No.: PCT/CN2004/001330
§ 371 (c)(1),
(2), (4) Date: Oct. 24, 2008

(87) PCT Pub. No.: WO2006/021131
PCT Pub. Date: Mar. 2, 2006

(65) Prior Publication Data
US 2010/0151448 A1    Jun. 17, 2010

(30) Foreign Application Priority Data
Aug. 26, 2004    (CN) .......................... 2004 1 0056866

(51) Int. Cl.
*C12Q 1/68*    (2006.01)
*C12P 19/34*    (2006.01)
(52) U.S. Cl.
USPC ........................................ 435/6.12; 435/91.2
(58) Field of Classification Search
None
See application file for complete search history.

(56) References Cited

U.S. PATENT DOCUMENTS

| | | | |
|---|---|---|---|
| 5,882,856 A | 3/1999 | Shuber | |
| 2003/0152925 A1 | 8/2003 | Chun | |
| 2003/0219751 A1 | 11/2003 | Lao et al. | |
| 2004/0053254 A1* | 3/2004 | Wangh et al. ................ | 435/6 |
| 2004/0110182 A1 | 6/2004 | Koizumi et al. | |
| 2004/0146866 A1 | 7/2004 | Fu | |
| 2004/0235032 A1* | 11/2004 | Suzuki et al. ................ | 435/6 |
| 2006/0205006 A1* | 9/2006 | Godfrey et al. .............. | 435/6 |
| 2007/0059700 A1 | 3/2007 | Tao et al. | |

FOREIGN PATENT DOCUMENTS

| | | |
|---|---|---|
| CN | 1287176 A | 3/2001 |
| CN | 1496413 A | 5/2004 |
| CN | 1515684 A | 7/2004 |
| JP | 11-507226 A | 6/1999 |
| JP | 11-332597 A | 12/1999 |
| JP | 2000-201697 A | 7/2000 |
| JP | 2003-199568 A | 7/2003 |
| WO | WO-96/41012 A1 | 12/1996 |
| WO | WO-02/057479 A2 | 7/2002 |
| WO | WO-02/057479 A3 | 7/2002 |
| WO | WO-02/083948 A1 | 10/2002 |
| WO | WO-02/090561 A1 | 11/2002 |
| WO | WO-03/023055 A2 | 3/2003 |
| WO | WO-03/023055 A3 | 3/2003 |
| WO | WO-2004/065628 A1 | 8/2004 |
| WO | WO-2004/099439 A1 | 11/2004 |

OTHER PUBLICATIONS

Sanchez, J.A. et al. (Feb. 17, 2004). "Linear-After-The Exponential (LATE)—PCR: An Advanced Method of Asymmetric PCR and its Uses in Quantitative Real-Time Analysis," *Proc. Natl. Acad. Sci. USA* 101(7):1933-1938.
Alizadeh, A.A. at al. (Feb. 3, 2000). "Distinct Types of Diffuse Large B-Cell Lymphoma Identified by Gene Expression Profiling," *Nature* 403(6769):503-511.
Andras, S.C. et al. (Sep. 2001). "Strategies for Signal Amplification in Nucleic Acid Detection," *Mol. Biotechnol.* 19(1):29-44.
Debouck, C. et al. (Jan. 1999). "DNA Microarrays in Drug Discovery and Development," *Nature Genetics Supplement* 21(1):48-50.
Dickman, M. et al. (Aug. 15, 2000). "Isolation of Single-Stranded DNA Using Denaturing DNA Chromatography," *Anal. Biochem.* 284(1):164-167.
Duggan, D.L. et al. (Jan. 1999). "Expression Profiling Using cDNA Microarrays," *Nature Genetics Supplement* 21(1):10-14.
Erdogan, F. et al. (2001). "Detection of Mitochondrial Single Nucleotide Polymorphisms Using a Primer Elongation Reaction on Oligonucleotide Microarrays," *Nucleic Acids Res.* 29(7e36):1-7.
Espelund, M. et al. (Oct. 25, 1990). "A Simple Method for Generating Single-Stranded DNA Probes Labeled to High Activities," *Nucleic Acids Res.* 18(20):6157-6158.
Gao, H. et al. (2003). "Comparison of Different Methods for Preparing Single Stranded DNA for Oligonucleotide Microarray," *Analytical Letters* 33(13):2849-2863.
Gerhold, D. et al. (May 1999). "DNA Chips: Promising Toys Have Become Powerful Tools," *Trends Biochem. Sci.* 24:168-173.
Gorelov, V.N. et al. (Apr. 15, 1994). "A Method to Increase the Sensitivity of Mutation Specific Oligonucleotide Hybridization Using Asymmetric Polymerase-Chain Reaction (PCR)," *Biochem. Biophys. Res. Commun.* 200(1):365-369.

(Continued)

*Primary Examiner* — Kenneth R. Horlick
*Assistant Examiner* — David Thomas
(74) *Attorney, Agent, or Firm* — Morrison & Foerster LLP

(57) ABSTRACT

The present invention discloses an asymmetric PCR amplification method, its special primer and application, aims to provide a simple, effective PCR amplification for preparation of single-stranded product. The asymmetric PCR primer of the invention comprises some PCR primer pairs, in which an unrelated nucleic acids sequence to target sequence to be detected is added onto 5'-terminal of one primer. The asymmetric PCR amplification provided includes the steps: 1) preparative denaturing; 2) repetitiously denaturing, primers annealing, extending cycles as the first stage of PCR amplification; 3) repetitiously denaturing, primer extending cycles as the second stage of PCR amplification, wherein an unrelated nucleic acids sequence to target sequence to be detected is added onto 5'-terminal of one PCR primer of each pair in extension. With the asymmetric PCR amplification of the invention, high throughput of single-stranded products can be obtained, single PCR amplification or multiple PCR amplification can be carried out. And the method can be widely used in detection of nucleic acids.

9 Claims, 7 Drawing Sheets

(56) References Cited

OTHER PUBLICATIONS

Guo, X. et al. (Sep. 2003). "Detection of Dengue Virus Replicative Intermmediate and Replicative Form RNA with Single Strand DNA Hybridization Probes Generated by Asymmetric PCR," *Acta. Parasitol. Med. Entomol. Sin.* 10(3):157-162 (Abstract Only in English.).

Guo, Z. et al. (Mar. 2002). "Oligonucleotide Arrays for High-Throughput SNPs Detection in the MHC Class I Genes: HLA-B as a Model System," *Genome Res.* 12(3):447-457.

Gyllensten, U.B. et al. (Oct. 1988). "Generation of Single-Stranded DNA by the Polymerase Chain Reaction and its Application to Direct Sequencing of the *HLA-DQA* Locus," *Proc. Natl. Acad. Sci. USA* 85(20):7652-7656.

He, Z. et al. (Mar. 2002). "Establishment and Preliminary Application of Oligonucleotide Microarray in IGF—II Gene SNP Analyzing and Genotyping," *Chinese Journal of Sports Med.* 21(2):116-121 (Abstract Only in English.).

Higuchi, R.G. et al. (1989). "Production of Single-Stranded DNA Templates by Exonuclease Digestion Following the Polymerase Chain Reaction," *Nucleic Acid Res.* 17(14):5865.

Hughes, T.R. et al. (Apr. 2001). "Expression Profiling Using Mircoarrays Fabricated by an Ink-Jet Oligonucleotide Synthesizer," *Nat. Biotechnol.* 19(4):342-347.

International Search Report mailed May 26, 2005, for PCT Application No. PCT/CN2004/001330, filed Nov. 22, 2004, six pages (English translation, three pages of document.).

Karsten, S.L. et al. (2002). "An Evaluation of Tyramide Signal Amplification and Archived Fixed and Frozen Tissue in Mircoarray Gene Expression Analysis," *Nucleic Acids Res.* 30(2-e4):1-9.

Kawai, S. et al. (Feb. 15, 1993). "A Simple Method of Detecting Amplified DNA with Immobilized Probes on Microtiter Wells," *Anal. Biochem.* 209(1):63-69.

Kricka, L.J. (1999). "Nucleic Acid Detection Technologies—Labels, Strategies, and Formats," *Clin. Chem.* 45(4):453-458.

Li, S-D. et al. (2003). "Fabrication and Optimization of HLA-DRB1-12 Oligonucleotide Microarray," *Chinese Journal of Experimental Hematology* 11(4):393-397.

Peng, X. et al. (Aug. 2002). "Synthesis of Single-Stranded DNA Probe Using Technique of Primer Length-Asymmetric PCR," *Chin. J. Lab. Diagn.* 6(4):206-208 (Abstract only in English.).

Scott, D.L. et al. (Jul. 1998). "The Differentiation of *Phytophthora* Species that are Pathogenic on Potatoes by an Asymmetric PCR Combined with Single-Strand Conformation Polymorphism Analysis," *Lett. Appl. Microbiol.* 27(1):39-44.

Su, Y-H. et al. (Dec. 2000). "Cloning Full Length cDNA Representing Difference Products Without Screening the Library," *Chin. J. Biochem. Mol. Biol.* 16(6):751-754 (Abstract only in English.).

Zhou, J. et al. (2003). "Development and Preliminary Application of the Genechip for Detection of *Schistosoma japonicum*," *Chinese Journal of Pest Control* 19(9):524-527, Translation of Abstract only, one page.

\* cited by examiner

|   | 1 | 2 | 3 | 4 | 5 | 6 | 7 | 8 | 9 |
|---|---|---|---|---|---|---|---|---|---|
| A | 090 QC | 090 QC | 090 QC | | | | | | |
| B | 001 generic | 001 generic | 001 generic | 075 generic | 075 generic | 075 generic | | | |
| C | 024 G+ | 024 G+ | 024 G+ | | | | | | |
| D | 053 *staphyl.* | 053 *staphyl.* | 053 *staphyl.* | | | | | | |
| E | 002 *aureus* | 002 *aureus* | 002 *aureus* | | | | | | |
| F | | | | | | | | | |
| G | | | | | | | | | |
| H | | | | | | | | | |
| I | | | | | | | 090 QC | 090 QC | 090 QC |

Figure 2 system A system B system C 26001　　　　　　　26001　　　　　　blank control
　　　　　　　repeat 1　　　　　　repeat 2

|   | 1 | 2 | 3 | 4 | 5 | 6 |
|---|---|---|---|---|---|---|
| A |   |   |   | 654 23S | 654 23S | 654 23S |
| B | 656 tetK | 656 tetK | 656 tetK | 657 tetK | 657 tetK | 657 tetK |
| C | 658 tetM | 658 tetM | 658 tetM | 659 tetM | 659 tetM | 659 tetM |
| D | 660 ermA | 660 ermA | 660 ermA | 661 ermA | 661 ermA | 661 ermA |
| E | 662 ermC | 662 ermC | 662 ermC | 663 ermC | 663 ermC | 663 ermC |
| F | 655 23S | 655 23S | 655 23S |   |   |   |

ASYMMETRIC PCR AMPLIFICATION, ITS SPECIAL PRIMER AND APPLICATION

CROSS-REFERENCE TO RELATED APPLICATIONS

This application is a National Phase filing under 35 U.S.C. §371 of International Application No. PCT/CN2004/001330 having an International Filing Date of Nov. 22, 2004, which claims priority to Chinese Patent Application No. 200410056866.0, filed on Aug. 26, 2004, the contents of each of which are incorporated herein by reference in their entirety.

TECHNICAL FIELD

This application relates to PCR amplification methods, primers for PCR amplification methods, and uses thereof. In particular, the application relates to asymmetric PCR amplification, primers for asymmetric PCR amplification, and uses thereof in detection of nucleic acids.

BACKGROUND

As life science research advances, it becomes well-recognized that nucleic acid is the key substance for the determination of genetic information. By determining changes or mutations in the nucleic acid sequences in a sample of a subject, one can determine whether the subject carries pathogenic microbes and/or resistance to such microbes, whether the subject has certain diseases, and whether the subject is under certain genetic state. Therefore, nucleic acid analysis techniques find application in various areas of life science research, including testing, classification, and detection of drug resistance genes of pathogenic microbes, diagnosis and prognosis of diseases, HLA classification, and SNP detection.

Because the amount of nucleic acid in a sample is usually insufficient for analysis, it is usually necessary to amplify the nucleic acid to be detected prior to the analysis. Methods of amplification include polymeric chain reactions (PCR), reverse transcription polymeric chain reaction (RT-PCR), strand displacement amplification (RDA), and rolling circle amplification (RCA). Andras et al., *Mol. Biotechnol.*, 19:29-44, 2001. Among those, PCR is currently used most often. There are many methods for analyzing PCR products. For example, agarose gel electrophoresis or PAGE electrophoresis have been used for detection of PCR products. These electrophoresis methods provide fast and convenience analyses. However, these methods suffer from low specificity and are thus unsuitable for gene mutation analyses. Another method for analyzing PCR products is use of restriction endonuclease, which has limited application, low sensitivity, and is hard to operate. One method that ensures accuracy in sequence information of PCR product involves cloning the PCR product and sequencing the cloned sequence. That method, however, involves multiple steps and is thus costly and non-practical.

Methods for hybridization of PCR products with probes include: 1) Southern hybridization, i.e., use electrophoresis to separate out the PCR products, transfer the PCR product to a membrane, and hybridize the PCR products with a labeled probe. This technology produces good specificity, but is complicated in operation, time consuming, and thus not suitable for parallel analysis of multiple features. 2) Positive dot hybridization, i.e., immobilize PCR products on the surfaces of a membrane or other solid substrates and hybridize the immobilized PCR products with a probe. This method requires that the PCR products be purified, quantitated, and immobilized, and is time consuming and unsuitable for detection in small amounts of samples. 3) reverse dot hybridization, i.e., hybridize the PCR products to probes that are previously immobilized to the surface of a membrane or other solid substrates. A substrate containing a large number of probes can be prepared ahead of time, and can be used to analyze PCR products immediately after the completion of the PCR reactions. The method is thus fast and convenient, and is suitable for use in kits and gene chips.

Gene chip technology is revolutionary. Due to its systematic, microdized, and automatic characteristics, gene chip technology finds important applications in nucleic acid analyses, particularly in high throughput nucleic acid analyses. Debouck and Goodfellow, *Nature Genetics*, 1999, 21 (Suppl.):48-50; Duggan et al., *Nature Genetics*, 1999, 21 (Suppl.):10-14; Gerhold et al., *Trends Biochem. Sci.*, 1999, 24:168-173; and Alizadeh et al., *Nature*, 2000, 403:503-511. Nucleic acid chips have been used to analyze gene expression profiles under specific conditions, and have also been used to determine single nucleotide polymorphism (SNP) in gene regions that are up to 1 kb. Guo et al., *Genome Res.*, 2002, 12:447-57.

Traditional passive nucleic acid analysis using biochips (for example biochips used for detection of infectious diseases) typically include three separate steps. The first step is sample preparation, i.e., preparation of nucleic acids from samples such as plasma, blood, saliva, urine, and feces. The nucleic acids obtained from such samples are usually insufficient to be analyzed directly, and need further amplification, such as PCR amplification. The second step is nucleic acid hybridization, i.e., hybridization between the amplified product and the probes immobilized on the chip. The third step is detection of hybridization signals, which is typically carried out by detection of certain labels, which can be introduced during the process of amplification and hybridization. The method of detection depends on the labels that are used. For example, fluorescence detector can be used to detect fluorescent labels, while autoradiograms can be used to detect radiolabels. In cases where biotin and straptavidin labels are used, further enzymatic amplification can be carried out. Different amplification methods are used depending on the desired sensitivity of the experiment. For example, Tyramide signal amplification (TSA) and branched DNA methods as described in Karsten et al., *Nucleic Acids Res.*, 2002, E4 and Kricka, *Clin. Chem.*, 1999, 45:453-458, respectively.

Hybridization between target nucleic acid and probes immobilized on the surface of the biochip constitutes a central step in the nucleic acid detection. The target nucleic acid is typically amplified by PCR, denatured into single-chain PCR products, which are in turn hybridized to probes under stringent conditions. The hybridized product is then washed and detected. During hybridization, only one chain of the PCR product can hybridize with the probe. The corresponding complement chain may interfere with the hybridization due to self-annealing of the PCR double chain product. As a result, hybridization signals may be lost. It has been found that, when hybridized to an oligonucleotide probe, the hybridization sensitivity of a single chain DNA is about five times higher than that of denatured double-stranded DNA. Kawai et al., *Anal. Biochem.* 1993, 209:63-69. Thus, it is desirable to obtain single chain nucleic acid for high efficiency hybridization with oligonucleotide probes on gene chips.

There are several methods of preparing for single chain nucleic acid. In addition to denaturation of double stranded DNA by heat or base, methods of preparing single chain nucleic acid include the following.

1. The reverse transcription method. In this method, a T7 promoter is added to a PCR primer. A single chain nucleic acid is produced by T7 RNA-polymerase-mediated in vitro transcription using purified PCR product as a template. Hughes et al., *Nat. Biotechnol.*, 2001, 19:342-347. Although the yield of single chain nucleic acid is quite high with this method, such two-step method is inconvenient and prone to contamination by RNAase.

2. Exonuclease cleavage method, Higuchi and Ochman, *Nucleic Acid Res.*, 1989, 17:5865. In this method, one of the PCR primers is phosphorylated. When the PCR product is subject to cleavage by an exonuclease, the chain that extends from the phosphorylated primer would not be cleaved. The exonuclease will then have to be heat inactivated. This method requires purification of PCR products and relies on exonuclease activity, and is thus inconvenient.

4. Denaturing high-performance liquid chromatography (DHPLC). In this method, one of the PCR primers is labeled with biotin. The chain that extends from the labeled primer can therefore be separated from the other chain in DHPLC. Dickman and Hornby, *Anal. Biochem.*, 2000, 284:164-167. The desired single chain can be obtained from the double stranded PCR product within 15 minutes. Such method, however, requires expensive machinery and thus cannot be commonly used.

4. Magnetic bead capturing method. In this method, biotin is attached to one of the PCR primers. The chain that extends from the labeled primer can be captured by straptavidin-coated magnetic beads, and dissociated from the beads using NaOH. Espelund, et al., *Nucleic Acids Res.*, 1990, 18:6157-6158. This method is very expensive due to the use of coated magnetic beads.

5. Asymmetric PCR. While all the above methods involve extra steps after the PCR reactions, asymmetric PCR allows preparation of DNA during the PCR reaction process. We found that both asymmetric PCR and magnetic bead capturing method produce relatively high sensitivity and specificity, while heat denaturation and base denaturation methods often produce false negative results. Among all these methods, asymmetric PCR is relatively simple and low cost, and is thus much more practical. Gao et al., *Analytical Letters*, 2003, 33:2849-2863.

Currently, there are the following schemes for asymmetric PCR.

1) Use different concentrations of upstream and downstream primers for asymmetric PCR. As the cycles increase, primers with a lower concentration are used up, while primers with a high concentration continue to produce single chain DNA at a linearly increasing rate. Gyllensten and Erlich, *Proc. Natl. Acad. Sci. U.S.A.*, 1988, 85:7652-7656. Similarly, Zihong He et al. used primers at a 1:10 and 1:20 ratio to asymmetrically amplify IGF-II genes for SNP detections. He et al., *Chinese Journal of Sports Medicine*, 2002, 21:116-121. Shuangding Li et al. used primers at ratio of 1:15 to asymmetrically amplify HLA-DRB1 gene. Li et al., *Chinese Journal of Experimental Hematology*, 2003, 11:393-397. Such method requires optimization of the ratio between upstream and downstream primers, and increases possibility of nonspecific amplification. As a result, the product is usually shown as a diffused band on electrophoresis. Erdogan et al., *Nucleic Acids Res.*, 2001, 29:E36.

2) Use different lengths of upstream and downstream primers for asymmetric PCR. Xiaomou Peng et al. used a 34-nucleotide upstream primer and a 20-nucleotide downstream primer to asymmetrically amplify the S gene of HBV. During the second phase of the PCR cycles, the annealing temperature is increased. The short primers are unable to anneal under such conditions, while the long primers continue to extend to obtain single chain nucleic acid. Peng et al., *Chinese Experimental Diagnostics*, 2002, 6:206-208. Although the primers are gene-specific, the use of long primers introduces nonspecificity in amplification. Such method is therefore not suitable for the amplification of genes with many SNP sites (such as bacterial 16S rRNA gene).

3) Use of symmetric PCR to generate a PCR template, and use a single primer or an unequal amount of to further asymmetrically amplify and label the PCR product. Gorelov et al., *Biochem. Biophys. Res. Commun.*, 1994, 200:365-369; Scott et al., *Lett. Appl. Microbiol.*, 1998, 27:39-44; Guo et al., *Genome Res.*, 2002, 12:447-457; Zhou et al., *Medical Animal Control*, 2003, 19:524-527. These methods use purified symmetric PCR product as a template, and subsequently use single primer to produce single chain via PCR cycles. The method requires multiple steps of reactions, and is therefore time consuming and inconvenient.

Traditional methods of multiplex PCR require multiple levels of optimizations. These methods have the following problems. 1) The use of multiple primers generates false positive amplification by these different primers. 2) Competition among the different primers create unbalanced amplification of the target nucleic acids, that is, certain primer pairs amplify efficiently while certain primer pairs amplify very inefficiently. 3) It is different to repeat the experiment. It therefore will be even more unsatisfactory to further carry out asymmetric PCR under such circumstances. The methods described above are therefore not suitable for the simultaneous analysis of multiple targets. There is a need for single-step asymmetric PCR.

DISCLOSURE OF THE INVENTION

The present invention provides a simple and efficient asymmetric PCR amplification method for the preparation of single chain amplification products and primers for such method.

The present invention provides primer sets for asymmetric PCR amplification, comprising several PCR primer pairs, wherein one of the two primers in each primer pair has at its 5' end an oligonucleotide tail having a sequence that is unrelated to the target sequence to be amplified.

In order for the primers to have a suitable Tm value, the oligonucleotide tail described herein is usually between 8-40 bp, preferably 15-25 bp.

To balanced the amplification efficiencies among the different target sequences, also provided among the asymmetric PCR primers is a generic primer, wherein at least 8 continuous nucleotides of the generic primer is the same as those in the oligonucleotide tail. Preferably, the generic primer has the same sequence as that of the oligonucleotide tail.

To facilitate asymmetric amplification and generation of single chains, the concentration of the generic primer described herein is higher than that of the gene specific primer pairs described herein.

The invention thus provides a method of asymmetric PCR amplification using asymmetric PCR primers, wherein the method comprises the steps of: 1) predenaturation; 2) a first phase of PCR amplification comprising one or more cycles of denaturation, annealing, and primer extension; and 3) a second phase of PCR amplification comprising one or more cycles of denaturation, annealing, and primer extension, wherein one of the two primers in the primer pairs for primer extension has at its 5' end an oligonucleotide tail having a sequence that is unrelated to the target sequence.

In order to increase amplification efficiency, an additional primer extension reaction is carried out after the second phase of PCR amplification.

The first phase of PCR reaction in step 2) above can have 15-25 cycles, and the extension temperature for the second phase of PCR in step 3) can be 60-75° C.

The asymmetric PCR reaction method of the present invention is further illustrated in FIG. 1. In FIG. 1, sf-1/sr-1 and sf-2/sr-2 are specific primer pairs for target gene 1 and target gene 2, respectively. Among these, sr-1 and sr-2 have at their 5' end a generic sequence. "Up" refers to the generic primer, whose sequence is the same as the generic sequence in sr-1 and sr-2. During the asymmetric PCR amplification reaction, the DNA polymerase, dNTP, $Mg^{2+}$, and reaction buffer in the reaction mixture are the same as those used for traditional PCR, and the condition can be optimized based on the requirements of different reactions.

The asymmetric PCR amplification reaction of the present invention has two phases. The first phase of PCR is the same as traditional PCR, and includes the steps of denaturation, primer annealing, and primer extension. The annealing temperature can be adjusted based on the Tm of the gene specific primers. Similarly, the extension time depends on the length of the fragment to be amplified. Both primers are used during the traditional amplification. In the second phase of the PCR amplification, the temperature for primer annealing is the same as the temperature for primer extension. The second phase therefore only has the steps of denaturation and primer extension. Only the primers with tails, which are longer and thus have higher $T_m$, can anneal and extend, thereby produce single chains.

The generic primers used in the asymmetric PCR method of the present invention have the following functions. During the first phase of PCR, the generic primer can participate in the amplification reaction after the second temperature cycles, thereby balances the amplification efficiency of different targets in a multiplex amplification reaction. Due to the high concentration of the generic primer, it balances out the differences in concentration of different primers throughout the entire amplification process, thereby facilitates asymmetric amplification and creation of single chains.

Another purpose of the present invention is to provide a use of asymmetric PCR primers in the detection of nucleic acid.

The asymmetric PCR primers described in the present invention are useful for multiple asymmetric PCT amplifications, followed by gene chip detection or other hybridization methods such as membrane hybridization, which allows detection of multiple target sequences conveniently.

The asymmetric PCR products generated by methods of the present invention can be used for the following gene chip detection methods: a) reverse hybridization, i.e., mix the product of asymmetric PCR amplification with hybridization buffer, heat denature, and hybridize with oligonucleotide probes immobilized on gene chips; or b) positive hybridization, i.e., purify the product of asymmetric PCR amplification, immobilize the purified product on the surface of a solid carrier to make gene chips, and hybridize the gene chip with nucleic acid probes. At the end of the hybridization, different labeling methods and signal detection methods can be used to detect the hybridization signal and complete the detection of the target sequence.

The asymmetric PCR method of the present invention has the following advantages over traditional asymmetric PCR methods:

1) The addition of a generic sequence that is unrelated to the target sequence at the 5' end of one primer of the primer pairs make one primer in the primer pair longer than the other primer, thus differentiates the Tm of the two primers in the primer pair. The generic sequence on the 5' end oligonucleotide tail also deemphasizes the differences among the gene specific sequences, increases the amplification frequency of the initial PCR cycles, and overcomes the difficulties in primer design.

2) The addition of a generic primer having the same sequence as that of the oligonucleotide tail creates a further imbalance in primer numbers between the upstream and down stream primers.

3) More importantly, the asymmetric PCR primers of the present invention can be used for multiplex PCR amplification without the need for complicated optimization process. There are two reasons for this advantage. First, because one out of two primer for all the primer pairs has the same generic sequence, amplification efficiency for these primer pairs tend to be similar and the possibility of interference among the different primers is low. Second, the generic primer balances the primers in the amplification process. If one particular gene specific primer pairs have low amplification efficiency, more generic primers will participate in the subsequent amplification reaction. The lower the amplification efficiency of the gene specific primers, the more generic primers that participate in the subsequent reaction, and vice versa. Therefore, different target molecules are amplified at about the same efficiency. The generic primer thus creates a balance among the different PCR reactions, and ensures similar amplification efficiency of all gene specific primers.

BRIEF DESCRIPTION OF THE FIGURES

FIG. 2 provides a schematic diagram of probe arrays used in Example 1.

FIG. 6 provides a schematic diagram of an array of probes as described in Example 2.

BEST MODE OF EXAMPLES OF THE PRESENT INVENTION

Example 1

Figure 1:
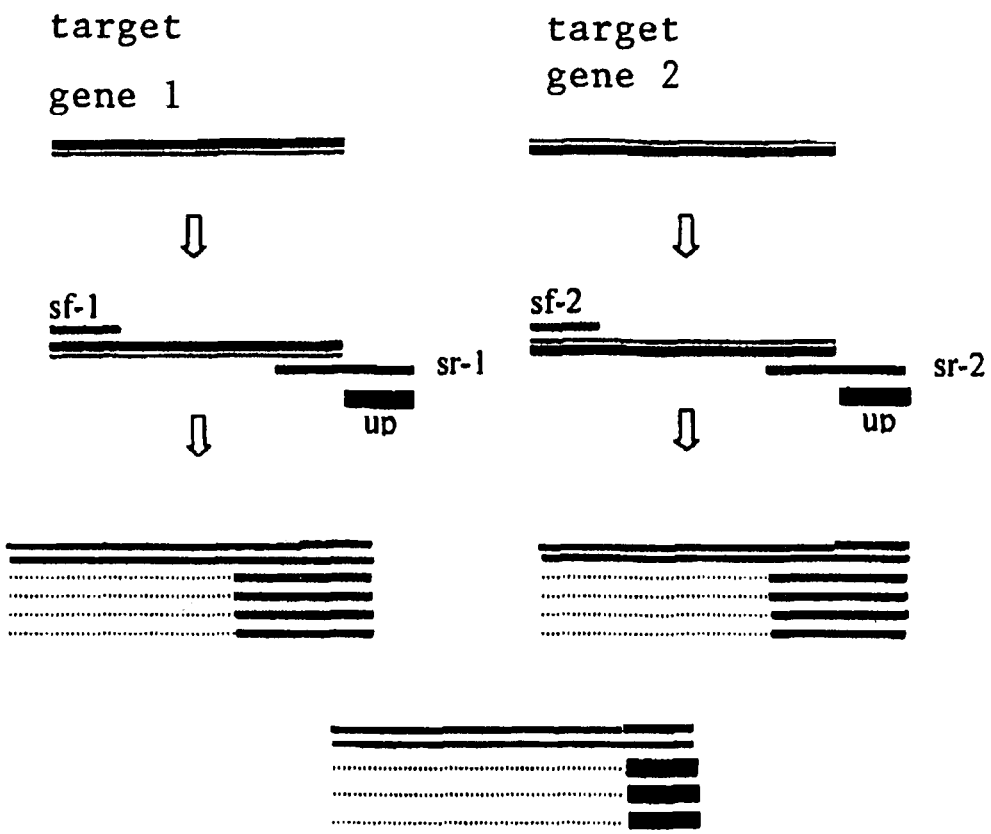
FIG. 1 provides a schematic diagram of an asymmetric PCR reaction of the present invention.

Single Asymmetric PCR Amplification and its Application in Determination of Gram-Positive Bacteria on Gene Chips 1. Gene Specific Primers for PCR Amplification and Various Oligonucleotide Probes Both primers and probes were synthesized by Shanghai Boya Biotechnology Company. Certain primers having at their 5' end a TAMRA fluorescent label and probes having at their 5' end a modifying amino group were also provided by Shanghai Boya Biotechnology Company.

The target sequence for gene specific primers was bacterial 16S rRNA gene. The amplification fragment was about 1.5 kb. The categories of the primers as well as their oligonucleotide sequences are provided in Table 1.

TABLE 1

PCR primers for bacteria determination

| Primer No. | Primer Category | Primer Sequence |
|---|---|---|
| PMB-0408047 | Generic Primer | TAMRA-GGTTTCGGATGTTACA GCGT (SEQ ID NO. 1) |
| PMB-0201034 | Gene specific upstream primer without a tail | TAMRA-AGAGTTTGATCCTGGC TCAG (SEQ ID NO. 2) |
| PMB-0201002 | Gene specific downstream primer without a tail | AAGGAGGTGATCCAGCC (SEQ ID NO. 3) |
| PMB-0201042 | Gene specific upstream primer with a tail | TAMARA-GGTTTCGGATGTTAC AGCGTAGAGTTTGATCCTGGCT CAG (SEQ ID NO. 4) |
| PMB-0201041 | Gene specific downstream primer with a tail | TCACTTGCTTCCGTTGAGGAAG GAGGTGATCCAGCC (SEQ ID NO. 5) |

Various oligonucleotide probes can hybridize to various sites on a single chain amplification product of the target bacteria. The sequence of the probes were identical to a fragment of the bacteria 16S rRNA gene. The nucleic acid sequence of some nucleic acid probes and their corresponding targets are provided in Table 2.

TABLE 2

Probes for bacterial determination.

| Probe No. | Target | Probe Sequence |
|---|---|---|
| PBB-0201001 | All bacteria | NH2-T12-GCTGCCTCCCGTAGGA GT (SEQ ID NO. 6) |
| PBB-0201002 | *Staphylococcus aureus* | NH2-T12-AGAAGCAAGCTTCTCG TCCG (SEQ ID NO. 7) |
| PBB-0201024 | Gram-positive bacteria | NH2-T12-GGGCATGATGATTTGA CGTC (SEQ ID NO. 8) |
| PBB-0201053 | *Staphylococcus* | NH2-T12-TCCTCCATATCTCTGC GCAT (SEQ ID NO. 9) |
| PBB-0201075 | All bacteria | NH2-T12-GACGGGCGGTGTGTAC A (SEQ ID NO. 10) |
| PBB-0201090 | Control probe | HEX-GCTGCCTCGGCAAGGAGT-NH2 (SEQ ID NO. 11) |

2. Preparation of Substrate with Aldehyde Groups

Submerge glass substrate in acid solution overnight at room temperature. Wash off the acid solution three times with tap water, three times with distilled water, one time soak-wash with deionized water, and one time wash with deionized water. The glass substrate was then dried by centrifugation, and baked at 110° C. for 15 minutes to dry the glass substrate completely. The glass substrate was then soaked in 1% APTES (3-aminopropyltriethoxysilane) in 95% ethanol, shaken at room temperature on a shaking bed for four hours. The glass substrate was then washed once and soak-washed once with 95% EtOH. The cleaned glass substrate was then placed in vacuum dryer under maximum vacuum (−0.08 Mpa-0.1 Mpa) with gas valve closed for 20 minutes at 110° C.

The glass substrate was then cooled down to room temperature and soaked in 12.5% glutaric dialdehyde solution (400 ml 12.5% glutaric dialdehyde solution, 100 ml 50% glutaric dialdehyde, 300 ml phosphate buffer (1 mol/L NaH2PO4 30 ml, 2.628 g NaCl), pH 7.0), and shaken under room temperature for four hours. The glass substrate was then taken out from the glutaric dialdehyde solution, washed with 3×SSC three times, deionized water two times, centrifuged to get rid of water, and dried at room temperature.

3. Preparation of Glass Substrate with Probes Immobilized on the Surface (Gene Chip)

Dissolve probes shown in Table 2 in 50% DMSO with a final concentration of 10 μmol/L. Spot the probes on the substrate as shown in FIG. 2 using Cartesian Spotting Instrument (Cartesian Technologies, Inc., CA, USA) (9×9, 090QC represents probe PBB-0201090). The spotted glass substrate was dried under room temperature overnight, soaked twice in 0.2% SDS at room temperature for two minutes each under vibrating conditions. The glass substrate was then washed twice with deionized water, soak-washed once with deionized water, and centrifuged to get rid of water. The glass substrate was then transferred to NaBH4 solution (1 g NaBH4 dissolved in 300 ml 1×PBS, then add 100 ml ethanol), and shaken slightly for 5 minutes. The glass substrate was then washed once with deionized water and soaked-washed once with deionized water (one minute each), and centrifuged to get rid of water.

4. Bacteria Culturing and Nucleic Acid Extraction

The *Staphylococcus aureus* 26001 used herein was obtained from Chinese Medical Bacterial Reservation Center, Institute of Chinese Medicinal and Biological Products.

On a sterile work station, inoculate bacteria on a MH (Mueller Hinton Agar Medium) culture slab to separate out single colonies. The slabs were incubated upside down in a 35° C. incubator for 24 hours.

Place 10 mg G1145 glass beads and 40 mg G1152 glass beads (Sigma) in a sterile 1.5 ml centrifuge tube, add 100 μl 1×TE. Use a flame-sterilized tweezer to grab a toothpick or tip, pick a single colony from the culture slab, rub the toothpick or the tip against the glass beads at the bottom of the tube so that enough bacteria were left in the tube. Throw the toothpick or tip in a waste jar containing bacteria-killing solutions, and close the centrifugation tube. Vortex the tube on a vortex mixer (TDX-1, Beijing Tongda) at maximum speed for 5 minutes. The centrifuge tube was then placed in a 95° C. water bath for 5 minutes, and stored at 4° C.

5. Nucleic Acid PCR Amplification

The PCR system was assembled as shown in Table 3. 1 μL bacterial sample prepared by shaking glass beads in the 26001 bacterial suspension was added to each of the A, B, and C systems. The total reaction volume was 25 μl.

The PCR reactions were carried out on PTC-200 cycler (MJ Research Inc.). Systems A and B used asymmetric PCR amplification cycling as shown in Table 4. System C used asymmetric PCR amplification cycling as shown in Table 5.

TABLE 3

PCR reaction systems.

| Reactants | Final concentration |
|---|---|
| System A: only upstream gene specific primers contain a tail | |
| MasterMix (Beijing Tianwei Times) | 1x |
| PMB-0201042 | 0.2 μmol/L |

TABLE 3-continued

PCR reaction systems.

| Reactants | Final concentration |
|---|---|
| PMB-0201002 | 0.2 μmol/L |
| PMB-0408047 | 1 μmol/L |
| System B: both upstream and downstream gene specific primers contain a tail | |
| MasterMix (Beijing Tianwei Times) | 1x |
| PMB-0201042 | 0.2 μmol/L |
| PMB-0201041 | 0.2 μmol/L |
| PMB-0408047 | 1 μmol/L |
| System C: neither upstream nor downstream gene specific primers contains a tail | |
| MasterMix (Beijing Tianwei Times) | 1x |
| PMB-0201034 | 0.2 μmol/L |
| PMB-0201002 | 0.2 μmol/L |

TABLE 4

Thermal cycles for asymmetric PCR

| Temperature (° C.) | 94 | 94 | 59 | 72 | 94 | 70 | 72 | 4 |
|---|---|---|---|---|---|---|---|---|
| Time (s) | 180 | 15 | 60 | 90 | 15 | 90 | 300 | — |
| Cycles | 1 | 20 | | | 20 | | 1 | 1 |
| Comments | Predenaturation | First phase of PCR | | | Second phase of PCR | | / | / |

TABLE 5

Thermal cycles for symmetric PCR

| Temperature (° C.) | 94 | 94 | 59 | 72 | 72 | 4 |
|---|---|---|---|---|---|---|
| Time (s) | 180 | 15 | 60 | 90 | 300 | — |
| Cycles | 1 | 30 | | | 1 | 1 |

6. Electrophoresis

Agarose gel electrophoresis was used to detect PCR amplification products. The concentration of the agarose was 1.5%. Each sample was 2 μL, electrophoresis was carried out under 50V/cm for 30 minutes.

7. Hybridization

The hybridization system was as shown in Table 6.

TABLE 6

Hybridization reaction system

| Component | Final concentration | Amount (μl) |
|---|---|---|
| H2O | / | 1.0 |
| 20xSSC | 2x | 1.8 |
| 50xDenhardt's | 5x | 1.8 |
| 50% sulphated polyglucosan | 10% | 3.6 |
| 4% SDS | 0.4% | 1.8 |
| PCR product | / | 8.0 |
| Total | / | 18.0 |

Add 200 μl distilled water in a HybriCassettes™ (Beijing Bo'ao Biochip, Ltd.) to prevent evaporation of the hybridization systems. Place glass substrate immobilized with reactants on the surface and coverslip (SmartCover™, Beijing Bo'ao Biochip, Ltd.) in the hybridization cassette. Heat the hybridization system to 95° C. and maintain at 95° C. for five minutes to allow denaturation of the PCR product. The mixture was then immediately cooled down on an ice-water bath. Take 13 μL hybridization system, add it to the gap between the substrate and the cover slip through a hole on the cover slip. Close the hybridization cassette, and allow hybridization to take place for 90 minutes. The chip was then taken out, soaked in 2xSSC, 0.2% SDS solution, and shaken for five minutes. The chip was then soak-washed with deionized water for two times, one minute each, and centrifuged to get rid of water. Two experiments were carried out with the PCR systems containing the Staphylococcus aureus 26001 sample.

8. Detection of Signals on Chip

Fluorescent signals on the chips were detected by using the GenePix4000B scanner (Axon Instruments, Inc., CA, USA). Wavelength 532 nm, PMT 600, and power 33%.

9. Analysis of Results

Figure 3:
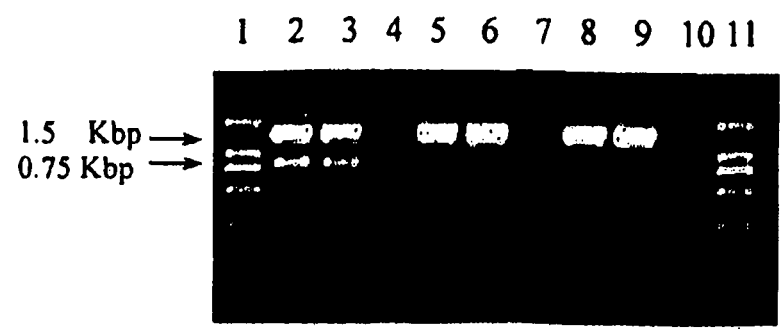
FIG. 3 provides an electrophoresis photograph of PCR products of Example 1.

Agarose gel electrophoresis results are shown in FIG. 3. Lanes 1 and 11 were DL2000 Marker (Takarar), lanes 2, 3, and 4 were System A PCR products; lanes 5, 6, and 7 were System B PCR products; lanes 8, 9, and 10 were System C PCR products. Among these lanes the PCR systems in lanes 2, 3, 5, 6, 8 and 9 contained 26001 bacterial sample, while the PCR systems in lanes 4, 7, and 10 contained blank controls.

As shown in FIG. 3, all three PCR systems (A, B, and C) produced good amplification of a double-stranded target nucleic acid that was about 1.5 kb, but only System A produced a clear single chain PCR amplification product.

Figure 4A:
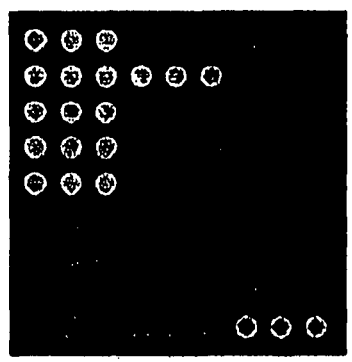
FIG. 4A provides a desired hybridization results with a *Staphylococcus aureus* 26001 sample as described in Example 1.
Figure 4B:
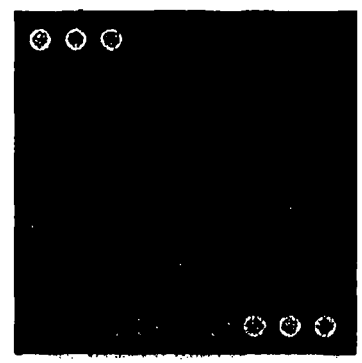
FIG. 4B provides a desired hybridization results with a blank control as described in Example 1.
Figure 5:
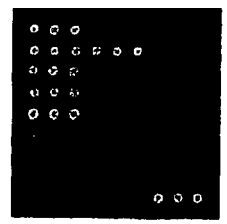
FIG. 5 provides results of fluorescent detection after hybridization.
Figure 5:
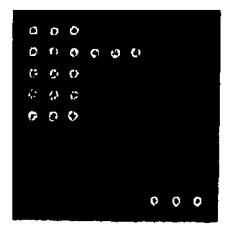
Figure 5:
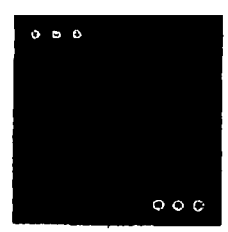
Figure 5:
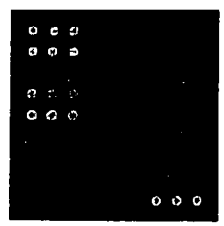
Figure 5:
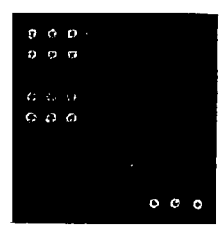
Figure 5:
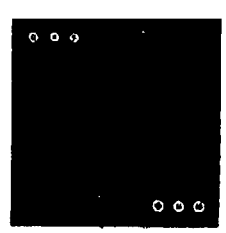
Figure 5:
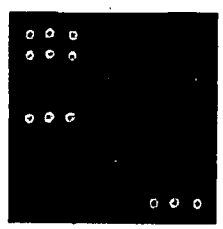
Figure 5:
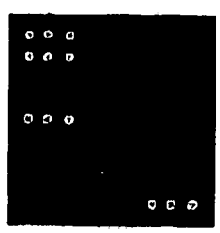
Figure 5:
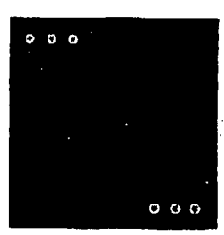

FIG. 4 shows positive hybridization results of experiments described herein. FIG. 4A shows the desired hybridization signal of Staphylococcus aureus; FIG. 4B shows the desired blank control signals; FIG. 5 shows fluorescent detection results of the hybridization experiment described herein. As shown in FIGS. 4 and 5, only the hybridization result using System A provides signals that match with FIG. 4, while the other two systems only produced partial results. One possible explanation is that the major products produced in Systems B and C were double stranded PCR products, which could self-anneal during hybridization, thereby weakens the positive signals or even fail to produce positive signals.

The electrophoresis and chip hybridization results demonstrated that the asymmetric PCR amplification system and asymmetric PCR amplification temperature cycles of the present invention are effective in preparation of single chain amplification products, which are particularly suitable for hybridization reactions, thereby significantly increased hybridization efficiency and hybridization signals.

Example 2

Detection of Bacterial Drug Resistance Genes Using Multiplex Asymmetric PCR Amplification and Gene Chips Both primers and probes were synthesized by Shanghai Boya Biotechnology Company. Certain primers having at their 5' end a TAMRA fluorescent label and probes having at their 5' end a modifying amino group were also provided by Shanghai Boya Biotechnology Company.

The categories of the gene specific primers, sequence information, target gene, and length of the amplified fragment are shown in Table 7. Each target gene has two probes, the sequence information of which is shown in Table 8. Among these, target genes tetK and tetM were tetracycline-resistant genes from gram-positive bacteria. Target genes ermA and ermC were macrolide-lincosamide-streptogramin B resistant genes from gram-positive bacteria. A section of the universal bacterial 23 rRNA gene was used as an internal control in order to monitor the PCR amplification and hybridization processes.

TABLE 7

Primers for detection of drug resistance genes

| Primer No. | Primer Category | Primer Sequence | Target Gene | Length of amplified fragment (bp) |
|---|---|---|---|---|
| PMB_0408101 | Upstream without tail | ATTCCGTTTATGCTTGGTTTGT (SEQ ID NO. 12) | tetK | 440 |
| PMB_0408121 | Downstream with tail | TAMRA-GGTTTCGGATGTTACAGCGTGCTATACCTGTTCCCTCTGAT (SEQ ID NO. 13) | | |
| PMB_0408103 | Upstream without tail | TACAGAATTAGGAAGCGTGGA (SEQ ID NO. 14) | tetM | 429 |
| PMB_0408122 | Downstream with tail | TAMRA-GGTTTCGGATGTTACAGCGTTCAGATTCGGTAAAGTTCGTC (SEQ ID NO. 15) | | |
| PMB_0408105 | Upstream without tail | CCTGTCGGAATTGGTTTTTAG (SEQ ID NO. 16) | ermA | 432 |
| PMB_0408123 | Downstream with tail | TAMRA-GGTTTCGGATGTTACAGCGTCGGTAAACCCCTCTGAGAATA (SEQ ID NO. 17) | | |
| PMB_0408107 | Upstream without tail | AGTAATGCCAATGAGCGTTTT (SEQ ID NO. 18) | ermC | 283 |
| PMB_0408124 | Downstream with tail | TAMRA-GGTTTCGGATGTTACAGCGTGGTGTAATTTCGTAACTGCCA (SEQ ID NO. 19) | | |
| PMB_0408115 | Upstream with tail | TAMRA-GGTTTCGGATGTTACAGCGTAACGGTCCTAAGGTAGCGAA (SEQ ID NO. 20) | 23S rRNA | 231 |
| PMB_0408116 | Downstream without tail | GGCTCCTACCTATCCTGTACA (SEQ ID NO. 21) | | |
| PMB_0408047 | Generic primer | TAMRA-GGTTTCGGATGTTACAGCGT (SEQ ID NO. 22) | | |

TABLE 8

Probes for drug resistance genes

| Probe No. | Target Gene | Probe Sequence (5'-3') |
|---|---|---|
| PBB-0204654 | 23S rRNA | NH2-T12-CGGGTAACCTGCATCTTCACA (SEQ ID NO. 23) |
| PBB-0204655 | 23S rRNA | NH2-T12-AYGGGGTCTTTCCGTCCGT (SEQ ID NO. 24) |
| PBB-0204656 | tetK | NH2-T12-GTTGCTTCTGGAATGAGTTTGCT (SEQ ID NO. 25) |
| PBB-0204657 | tetK | NH2-T12-TGTTATGGGCGGATTATCTTTTACT (SEQ ID NO. 26) |
| PBB-0204658 | tetM | NH2-T12-TTTCAGTGGGAAAATACGAAGGTG (SEQ ID NO. 27) |

TABLE 8-continued

Probes for drug resistance genes

| Probe No. | Target Gene | Probe Sequence (5'-3') |
|---|---|---|
| PBB-0204659 | tetM | NH2-T12-CATCATAGACACGCCAGGACATAT (SEQ ID NO. 28) |
| PBB-0204660 | ermA | NH2-T12-CAATCTTTTCGCAAATCCCTTCTC (SEQ ID NO. 29) |
| PBB-0204661 | ermA | NH2-T12-ATAGTAAACCCAAAGCTGTTGC (SEQ ID NO. 30) |
| PBB-0204662 | ermC | NH2-T12-TAGCAAACCCGTATTCCACGATT (SEQ ID NO. 31) |
| PBB-0204663 | ermC | NH2-T12-TTGGAAATTATCGTGATCAACAAGTT (SEQ ID NO. 32) |
| PBB-0201090 | Control probe | HEX-GCTGCCTCGGCAAGGAGT-NH2 (SEQ ID NO. 11) |

2. Preparation of Glass Substrate with Aldehyde Groups

Glass substrates with aldehyde groups are prepared as Example 1.

3. Preparation of Glass Substrate with Probes Immobilized on the Surface

The method of preparation was the same as Example 1. The probes are shown in Table 8. The probes were spotted as shown in FIG. 6 (6×6, 090QC refers to control probe PBB-0201090, the rest of the probes were numbered after the last three digits of the probe numbers. For example, PBB-024654 was represented as "654."

4. Bacterial Culture and Nucleic Acid Extraction

The sources of the bacteria used in the example are shown in Table 9. Bacterial culture and nucleic acid extraction methods are as shown in Example 2.

TABLE 9

Bacterial strains used in Example 2

| Source | Strain No. | Strain |
|---|---|---|
| Beijing Hospital | B435 | Staphylococcus aureus |
|  | B437 | Staphylococcus aureus |
| Beijing Tian Tan Hospital | MRSA6437 | Staphylococcus aureus |
|  | MRSA6460 | Staphylococcus aureus |
|  | MRSA6581 | Staphylococcus aureus |
| Beijing Tong Ren Hospital | TR1429 | Enterococcus faecalis |
|  | TR1887 | Enterococcus faecium |
|  | TR2041 | Staphylococcus epidermis |

5. PCR Amplification of Nucleic Acid

This example shows five different PCR amplifications in a single experiment. The PCR reaction systems were as shown below: 1× MaterMix (Beijing Tianwei Times); 0.2 µmol/L five pairs of gene specific primers as shown in Table 7; 1 µmol/L generic primer PMB_0408047; 1 µL bacterial sample after vibration with glass bead. The total reaction volume was 25 µL.

PCR was carried out on a PTC-200 (MJ Research Inc.) thermocycler. The asymmetric PCR thermal cycle was as shown in Table 4.

6. Hybridization and Detection

The hybridization reaction systems and methods and fluorescent detection methods after hybridization were as shown in Example 1.

7. Analysis of Results

Figure 7:
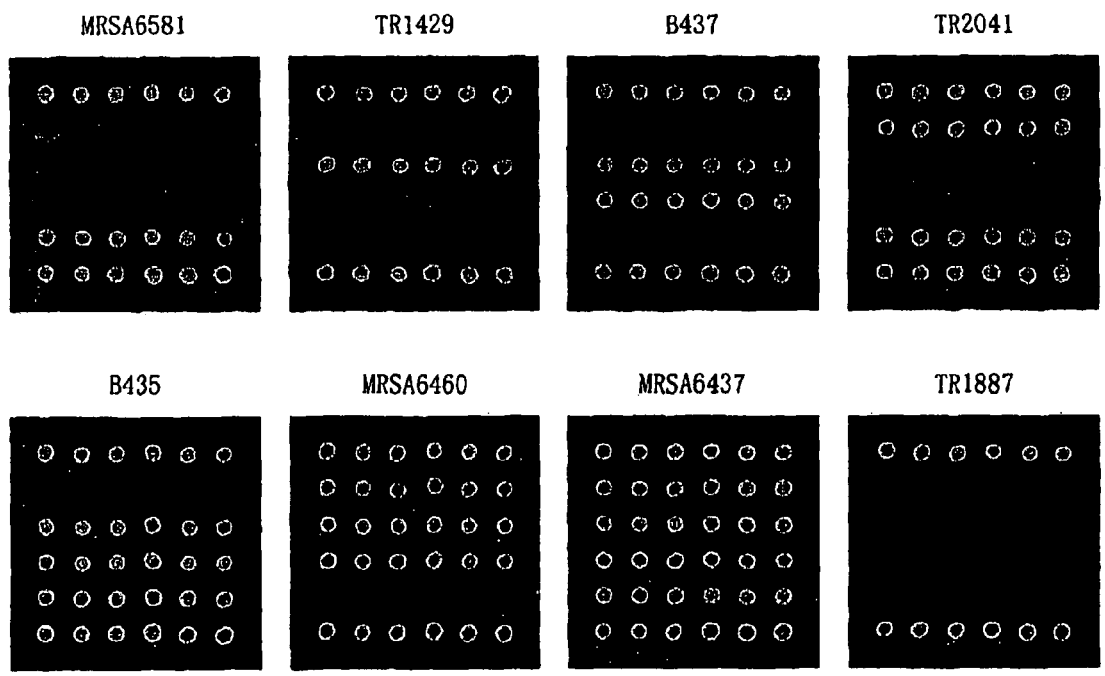
FIG. 7 provides results of fluorescent detection after hybridization as described in Example 2.

FIG. 7 shows the drug resistance gene detection results for 8 bacterial strains. As shown in FIG. 7, different bacterial strains have different kinds and numbers of drug resistance genes. *Staphylococcus aureus* MRSA6581 and *Enterococcus faecalis* only have one drug resistance gene. *Staphylococcus aureus* B437 and *Staphylococcus epidermis* TR2041 have two drug resistance genes. *Staphylococcus aureus* B435 and *Staphylococcus aureus* MRSA6460 have three drug resistance genes. *Staphylococcus aureus* MRSA6437 has four drug resistance genes. *Enterococcus faecium* has no drug resistance gene.

Furthermore, as shown in FIG. 7, the PCR and hybridization controls 23S rRNA gene worked well for all bacterial strains, producing good amplification and strong hybridization signals. Positive and homogeneous signals were obtained for all bacteria strains with one, two, three, or four drug resistance genes. This shows that the asymmetric PCR amplification method and temperature cycles of the present invention are suitable for parallel detection of multiple genes.

INDUSTRIAL APPLICATION

The asymmetric PCR amplification method of the present invention produces high yield of single chain product, which facilitates the ensuing hybridization reaction, improves hybridization efficiency, and increases hybridization signals. The method is also useful for single or multiple PCR amplifications under similar conditions without the necessity of optimization. The primers of the present invention are simple in design. The methods are easy to operate, and are applicable to multi-factor high throughput gene chip methods. The methods described herein can find use in microbe determination, classification, drug resistance gene detection, disease diagnosis and prognosis, HLA classification, SNP detection, as well as gene analyses.

What is claimed is:

1. An asymmetric PCR amplification method to produce single-stranded amplification products comprising amplification of a target nucleic acid sequence from a sample using primers and a DNA polymerase, wherein the method comprises the steps of:
   1) pre-denaturing the target nucleic acid sequence; and
   2) asymmetrically amplifying the target nucleic acid sequence by a PCR amplification reaction comprising
      i) a first phase of PCR amplification comprising one or more cycles of denaturation, primer annealing, and primer extension; and;
      ii) a second phase of PCR amplification comprising one or more cycles of denaturation, primer annealing, and primer extension,
   wherein the temperature for primer annealing and the temperature for primer extension in the second phase are the same, wherein the temperature for primer annealing in the second phase of PCR is higher than the temperature for primer annealing in the first phase of PCR, wherein the primers comprise a primer pair comprising a first primer and a second primer, wherein the first primer in the primer pair has at its 5' end an oligonucleotide tail having a sequence that is unrelated to the target sequence to be amplified, and wherein the $T_m$ of the first primer is greater than the $T_m$ of the second primer, thereby producing single-stranded amplification products.

2. The method according to claim 1, further comprising an additional extension step after the second phase of PCR amplification.

3. The method according to claim 1, wherein the number of PCR amplification cycles for the first phase of PCR amplification is 8-25.

4. The method according to claim 1, wherein the oligonucleotide tail is 8-40 nucleotides long.

5. The method according to claim 1, wherein the primers for PCR further comprise a generic primer, wherein the generic primer has at least 8 continuous nucleotides that are the same as those in the oligonucleotide tail.

6. The method according to claim 5, wherein the sequence of the generic primer is identical to that of the oligonucleotide tail.

7. The method according to claim 5, wherein the concentration of the generic primer is higher than that of the primer pair.

8. The method according to claim 1, wherein the extension temperature for the second phase of PCR is 60-75° C.

9. The method according to claim 1, wherein the first primer is longer than the second primer.

* * * * *

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1
<223> OTHER INFORMATION: Base 1 = linked to a TAMRA label

<400> SEQUENCE: 1
ggtttcggat gttacagcgt                                              20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1
```

-continued

<223> OTHER INFORMATION: Base 1 = linked to a TAMRA label

<400> SEQUENCE: 2
agagtttgat cctggctcag                                            20

<210> SEQ ID NO 3
<211> LENGTH: 17
<212> TYPE: DNA
<213> ORGANISM: Artificial Sequence
<220> FEATURE:
<223> OTHER INFORMATION: Oligonucleotide

<400> SEQUENCE: 3
aaggaggtga tccagcc                                               17

<210> SEQ ID NO 4
<211> LENGTH: 40
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1
<223> OTHER INFORMATION: Base 1 = linked to a TAMRA label

<400> SEQUENCE: 4
ggtttcggat gttacagcgt agagtttgat cctggctcag                      40

<210> SEQ ID NO 5
<211> LENGTH: 36
<212> TYPE: DNA
<213> ORGANISM: Artificial Sequence
<220> FEATURE:
<223> OTHER INFORMATION: Oligonucleotide

<400> SEQUENCE: 5
tcacttgctt ccgttgagga aggaggtgat ccagcc                          36

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide

<400> SEQUENCE: 6
tttttttttt ttgctgcctc ccgtaggagt                                 30

<210> SEQ ID NO 7
<211> LENGTH: 32
<212> TYPE: DNA
<213> ORGANISM: Artificial Sequence
<220> FEATURE:
<223> OTHER INFORMATION: Oligonucleotide

<400> SEQUENCE: 7
tttttttttt ttagaagcaa gcttctcgtc cg                              32

<210> SEQ ID NO 8
<211> LENGTH: 32
<212> TYPE: DNA
<213> ORGANISM: Artificial Sequence
<220> FEATURE:
<223> OTHER INFORMATION: Oligonucleotide

<400> SEQUENCE: 8

-continued ttttttttttt tgggcatga tgatttgacg tc                                    32

<210> SEQ ID NO 9
<211> LENGTH: 32
<212> TYPE: DNA
<213> ORGANISM: Artificial Sequence
<220> FEATURE:
<223> OTHER INFORMATION: Oligonucleotide

<400> SEQUENCE: 9 ttttttttttt ttcctccat atctctgcgc at                                    32

<210> SEQ ID NO 10
<211> LENGTH: 29
<212> TYPE: DNA
<213> ORGANISM: Artificial Sequence
<220> FEATURE:
<223> OTHER INFORMATION: Oligonucleotide

<400> SEQUENCE: 10 ttttttttttt tgacgggcg gtgtgtaca                                        29

<210> SEQ ID NO 11
<211> LENGTH: 18
<212> TYPE: DNA
<213> ORGANISM: Artificial Sequence
<220> FEATURE:
<223> OTHER INFORMATION: Oligonucleotide

<400> SEQUENCE: 11
gctgcctcgg caaggagt                                                    18

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide

<400> SEQUENCE: 12
attccgttta tgcttggttt gt                                               22

<210> SEQ ID NO 13
<211> LENGTH: 41
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1
<223> OTHER INFORMATION: Base 1 = linked to a TAMRA label

<400> SEQUENCE: 13
ggtttcggat gttacagcgt gctatacctg ttccctctga t                          41

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide

<400> SEQUENCE: 14
tacagaatta ggaagcgtgg a                                                21

<210> SEQ ID NO 15

```
<211> LENGTH: 41
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1
<223> OTHER INFORMATION: Base 1 = linked to a TAMRA label

<400> SEQUENCE: 15
ggtttcggat gttacagcgt tcagattcgg taaagttcgt c                41

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide

<400> SEQUENCE: 16
cctgtcggaa ttggtttta g                                       21

<210> SEQ ID NO 17
<211> LENGTH: 41
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1
<223> OTHER INFORMATION: Base 1 = linked to a TAMRA label

<400> SEQUENCE: 17
ggtttcggat gttacagcgt cggtaaaccc ctctgagaat a                41

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide

<400> SEQUENCE: 18
agtaatgcca atgagcgttt t                                      21

<210> SEQ ID NO 19
<211> LENGTH: 41
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1
<223> OTHER INFORMATION: Base 1 = linked to a TAMRA label

<400> SEQUENCE: 19
ggtttcggat gttacagcgt ggtgtaattt cgtaactgcc a                41

<210> SEQ ID NO 20
<211> LENGTH: 40
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1
```

-continued

<223> OTHER INFORMATION: Base 1 = linked to a TAMRA label

<400> SEQUENCE: 20
ggtttcggat gttacagcgt aacggtccta aggtagcgaa                    40

<210> SEQ ID NO 21
<211> LENGTH: 21
<212> TYPE: DNA
<213> ORGANISM: Artificial Sequence
<220> FEATURE:
<223> OTHER INFORMATION: Oligonucleotide

<400> SEQUENCE: 21
ggctcctacc tatcctgtac a                                       21

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 1
<223> OTHER INFORMATION: Base 1 = linked to a TAMRA label

<400> SEQUENCE: 22
ggtttcggat gttacagcgt                                         20

<210> SEQ ID NO 23
<211> LENGTH: 33
<212> TYPE: DNA
<213> ORGANISM: Artificial Sequence
<220> FEATURE:
<223> OTHER INFORMATION: Oligonucleotide

<400> SEQUENCE: 23
tttttttttt ttcgggtaac ctgcatcttc aca                          33

<210> SEQ ID NO 24
<211> LENGTH: 31
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 14
<223> OTHER INFORMATION: y = t or c

<400> SEQUENCE: 24
tttttttttt ttayggggtc tttccgtccg t                            31

<210> SEQ ID NO 25
<211> LENGTH: 35
<212> TYPE: DNA
<213> ORGANISM: Artificial Sequence
<220> FEATURE:
<223> OTHER INFORMATION: Oligonucleotide

<400> SEQUENCE: 25
tttttttttt ttgttgcttc tggaatgagt ttgct                        35

<210> SEQ ID NO 26
<211> LENGTH: 37
<212> TYPE: DNA
<213> ORGANISM: Artificial Sequence
<220> FEATURE:

<223> OTHER INFORMATION: Oligonucleotide

<400> SEQUENCE: 26
tttttttttt tttgttatgg gcggattatc ttttact         37

<210> SEQ ID NO 27
<211> LENGTH: 36
<212> TYPE: DNA
<213> ORGANISM: Artificial Sequence
<220> FEATURE:
<223> OTHER INFORMATION: Oligonucleotide

<400> SEQUENCE: 27
tttttttttt tttttcagtg ggaaaatacg aaggtg         36

<210> SEQ ID NO 28
<211> LENGTH: 36
<212> TYPE: DNA
<213> ORGANISM: Artificial Sequence
<220> FEATURE:
<223> OTHER INFORMATION: Oligonucleotide

<400> SEQUENCE: 28
tttttttttt ttcatcatag acacgccagg acatat         36

<210> SEQ ID NO 29
<211> LENGTH: 36
<212> TYPE: DNA
<213> ORGANISM: Artificial Sequence
<220> FEATURE:
<223> OTHER INFORMATION: Oligonucleotide

<400> SEQUENCE: 29
tttttttttt ttcaatcttt tcgcaaatcc cttctc         36

<210> SEQ ID NO 30
<211> LENGTH: 35
<212> TYPE: DNA
<213> ORGANISM: Artificial Sequence
<220> FEATURE:
<223> OTHER INFORMATION: Oligonucleotide

<400> SEQUENCE: 30
tttttttttt ttatagtaaa cccaaagctc gttgc         35

<210> SEQ ID NO 31
<211> LENGTH: 35
<212> TYPE: DNA
<213> ORGANISM: Artificial Sequence
<220> FEATURE:
<223> OTHER INFORMATION: Oligonucleotide

<400> SEQUENCE: 31
tttttttttt tttagcaaac ccgtattcca cgatt         35

<210> SEQ ID NO 32
<211> LENGTH: 38
<212> TYPE: DNA
<213> ORGANISM: Artificial Sequence
<220> FEATURE:
<223> OTHER INFORMATION: Oligonucleotide

<400> SEQUENCE: 32
tttttttttt ttttggaaat tatcgtgatc aacaagtt         38